United States Patent [19]

Nakamura et al.

[11] Patent Number: 4,898,935

[45] Date of Patent: Feb. 6, 1990

[54] METHOD OF PRODUCING SUCROSE FATTY ACID ESTER GRANULES

[75] Inventors: Shingo Nakamura, Kyoto; Hiroshi Nagahara, Osaka, both of Japan

[73] Assignee: Dai-Ichi Kogyo Seiyaku Co., Ltd., Kyoto, Japan

[21] Appl. No.: 297,806

[22] Filed: Jan. 17, 1989

[30] Foreign Application Priority Data

Jan. 22, 1988 [JP] Japan ................................ 63-6313247

[51] Int. Cl.$^4$ ........................ C07H 13/02; C07H 11/00
[52] U.S. Cl. ...................................... 536/119; 536/115
[58] Field of Search ................................ 536/119, 115

[56] References Cited

FOREIGN PATENT DOCUMENTS 45-3524  2/1970  Japan .
53-1249  1/1978  Japan .
54-32176 3/1979  Japan .

Primary Examiner—John W. Rollins
Assistant Examiner—Everett White
Attorney, Agent, or Firm—Jordan and Hamburg

[57] ABSTRACT

This invention relates to a method of producing sucrose fatty acid ester granules by the fluidized bed granulation and drying technique and consists in forming a fluidized bed comprising a sucrose fatty acid ester powder at a temperature not exceeding 60° C., spraying the fluidized bed with an aqueous sucrose fatty acid ester solution having a concentration of 3–20% by weight, as a binder, and then drying the sprayed fluidized bed, to thereby cause granulation. In accordance with the invention, the disintegration of sucrose fatty acid ester granules during granulation and drying can be prevented and highly pure sucrose fatty acid ester granules can be obtained. The sucrose fatty acid ester granules produced by the method of the invention are incapable of forming a cloud of fine powder, and have very good dispersibility and solubility.

1 Claim, No Drawings

METHOD OF PRODUCING SUCROSE FATTY ACID ESTER GRANULES

BACKGROUND OF THE INVENTION

This invention relates to a method of producing sucrose fatty acid ester (hereinafter sometimes referred to as "SE") granules by the fluidized bed granulation and drying technique.

Sucrose fatty acid esters (hereinafter sometimes referred to as "SEs") can be widely variegated in HLB value (hydrophile-lipophile balance value) and are used as nonionic surfactants in various fields. In particular, it is a recent trend to use them by preference as tasteless, odorless, nontoxic food additives.

Meanwhile, sucrose fatty acid esters currently on the market are mostly in the form of powders and, in some instances, in the form of aqueous solutions or lumps. No granulated SEs have been known as yet.

Such SE powders have a particle size distribution such that 90% or more can pass a 150-mesh sieve. Thus they contain a fine powder fraction in considerably large amounts. These SE powders are disadvantageous in:

(1) That, in handling them, the fine powder fraction rises as a cloud of dust;

(2) That, in the case of highly hydrophilic SEs, time is required for the dissolution thereof in water, since, on that occasion, SE particles stick together to form undissolved lumps; and (3) That said SE powders are poor in flowability.

Therefore, granular SEs which are easy to handle are desired. To date, a few proposals have been put forward for a method of granulating SEs or a method suggestive thereof.

Thus, for instance, Japanese Patent Publication No. 45-3524 proposes a method of producing granules which comprises allowing a powder to be granulated to fall spontaneously within a granulation column and come into contact with a gentle countercurrent of heated ordinary-pressure steam. However, when applied to a powdery SE, this method may allow the SE, which is a mixture of esters differing in the degree of esterification and has a wide melting range, to melt at temperatures not lower than 50° C. Conversely, at temperatures lower than 50° C., it is difficult to evaporate the moisture in the mass of particles moistened as a result of the use of steam at the granulation column height proposed, hence the powder is apt to cake.

Japanese Laid-Open Patent Publication KOKAI No. 54-32176 discloses a method of granulation and drying by the fluidized bed technique which comprises spraying a powder forming a fluidized bed with a binding agent. However, when water alone is used as the binding agent in carrying out this method for the granulation and drying of an SE, SE particles can grow to great granules but the granules are fragile and readily disintegrate upon collision with one another during drying. Although said method includes the use, as the binding agent, of a water-soluble macromolecular substance having great binding ability, such as CMC or PVA, the use of such binding agent decreases the purity of the SE, hence poses a restricted-use problem. Thus, the SE granules produced by this method cannot be regarded as food additive grade SEs as specified in the Japanese Food Additives Standards but can be used only as food additive compounds.

A granulation method disclosed in Japanese Patent Publication No. 53-1249 comprises adding a binding agent to an SE, kneading the mixture and then crushing the kneaded mixture. In this method, the frictional heat due to stirring in the steps of kneading and crushing readily causes a temperature rise, which results in melting or remelting of the SE. As a result, it is difficult to obtain granulation products desirable in size. Furthermore, when alcohol is used additionally as a binding agent, the working environment is contaminated and at the same time safety problems arise, for instance the alcohol vapor may catch fire.

Furthermore, the fact that no granulated SE products have been marketed until today is nothing but an implication that the granulation methods so far reported or proposed have problems in the practice thereof.

SUMMARY OF THE INVENTION

Accordingly, it is an object of the invention to provide a method of producing SE granules by which the above-mentioned problems in the prior art are overcome, in particular a method of producing SE granules by which the disintegration of SE granules in the granulation and drying steps can be prevented and highly pure SE granules can be obtained through the use of an aqueous SE solution, which has great binding capacity, as the binding agent.

The present invention provides a method of producing sucrose fatty acid ester granules by the fluidized bed granulation and drying technique which comprises forming a fluidized bed comprising a sucrose fatty acid ester powder at a temperature not exceeding 60° C., spraying the fluidized bed with an aqueous sucrose fatty acid ester solution having a concentration of 3–20% by weight, as a binder, and then drying the sprayed fluidized bed, to thereby cause granulation.

DETAILED DESCRIPTION OF PREFERRED EMBODIMENTS

The granulation technique to be used in the practice of the invention is not limited to any particular one provided that said technique falls under the category of the so-called fluidized bed granulation and drying technique.

The SE powder to be used in the practice of the invention is the product of esterification between sucrose and a fatty acid. The fatty acid preferably contains 12 to 22 carbon atoms. More preferably, said fatty acid should be a saturated one. The SE may be derived from a single fatty acid or a mixture of two or more fatty acids. The degree of esterification is not limited to any particular level.

The aqueous SE solution to be used as the binding agent is preferably an aqueous solution of the same ester as the SE powder to be granulated in accordance with the invention but may be different from the latter. An aqueous solution of an SE derived from an unsaturated fatty acid or acids may also be used.

This aqueous SE solution has great binding ability and therefore serves as a good binding agent in producing SE granules.

The concentration of this aqueous solution is 3 to 20% by weight, preferably 5 to 15% by weight. When the concentration of the aqueous solution is less than 3% by weight, the disintegration of granules in the steps of granulation and drying is difficult to prevent. When the concentration of the aqueous solution exceeds 20% by weight, the aqueous solution acquires an excessively high viscosity and becomes difficult to spray.

A granulation/drying temperature exceeding 60° C. may cause the SE to melt. At a temperature below 40° C., a fairly long time is required for drying. A temperature within the range of 45°–50° C. is particularly preferred.

The method of producing SE granules according to the invention as disclosed hereinabove can prevent the disintegration of SE granules during granulation and drying and never decreases the purity of SE granules. The granular SEs produced will not form a cloud of fine powder but have very good dispersibility and solubility.

The following examples and comparative examples illustrate the invention in further detail but are by no means limitative of the scope of the present invention.

In the following description, "%" means "% by weight".

EXAMPLE 1

A powdery SE (1,500 g; HLB value=11) derived from a constituent fatty acid mixture consisting of 70% stearic acid and 30% palmitic acid was charged into a fluidized bed drying apparatus (Granu-Glatt WSG-3; manufactured by Fuji Paudal Co., Ltd.) and caused to form a fluidized bed at a temperature of 45° C. with a warm air stream fed at a rate of about 1 m$^3$ per minute. Separately, a 10% aqueous solution of an SE (HLB value=11) was prepared. The powder in the fluidized bed was sprayed with 600 g of said aqueous solution at a rate of 45 g per minute, for granulation. After completion of the spraying, the fluidized bed was maintained for about 60 minutes for drying. Some properties of the SE granules obtained are shown in Table 1.

EXAMPLES 2 and 3

SEs having the same constituent fatty acid composition as but differing in HLB value from the SE used in Example 1 were used and SE granules were produced by following the procedure of Example 1 under the granulation and drying conditions shown in Table 1. The results obtained are shown in Table 1.

COMPARATIVE EXAMPLES 1–4

The same SE as used in Example 1 was used and fluidized bed drying was carried out under the granulation and drying conditions shown in Table 2. The results obtained are shown in Table 2.

In evaluating the grain size distribution and the dispersibility and solubility, the following methods were used.

(1) Grain size evaluation

The granulation products were evaluated in terms of grain size distribution according to the following criteria:

O: Not more than 20% passing a 150-mesh sieve.
Δ: 20–50% passing a 150-mesh sieve.
X: Not less than 50% passing a 150-mesh sieve.
XX: Failure in granulation due to melting and/or caking.

(2) Dispersibility and solubility

One gram of each granulation product was added to 200 ml of warm water (70° C.), the mixture was stirred at 200 rpm, and the time required for complete dissolution was measured. The dispersibility and solubility evaluation was made according to the following criteria:

O: Complete dissolution in 5 minutes.
Δ: Complete dissolution in 5–10 minutes.
X: Complete dissolution in 10–30 minutes.
XX: More than 30 minutes required for complete dissolution.

TABLE 1

| | Example 1 | Example 2 | Example 3 |
|---|---|---|---|
| Starting material: | | | |
| Sucrose fatty acid ester powder* | HBL value: 11 | HLB value: 2 | HLB value: 15 |
| Binder: | | | |
| Aqueous solution of sucrose fatty acid ester | HLB value: 11 | HLB value: 11 | HLB value: 15 |
| Concentration (%) | 10 | 15 | 5 |
| Granulation temperature (° C.) | 45 | 55 | 40 |
| Grain size evaluation | 0 | 0 | 0 |
| Dispersibility and solubility | 0 | 0 | 0 |
| Bulk specific gravity | 0.38 | 0.36 | 0.39 |
| Yield (%)** | 88.0 | 84.7 | 89.3 |

*90% or more passing a 150-mesh sieve.
** Ratio by weight of the amount of that part of SE granules obtained which does not pass a 150-mesh sieve to the amount of the starting SE material

TABLE 2

| | Comparative Example 1 | Comparative Example 2 | Comparative Example 3 | Comparative Example 4 |
|---|---|---|---|---|
| Starting material: | | | | |
| Sucrose fatty acid ester powder* | HLB value: 11 | HLB value: 11 | HLB value: 11 | HLB value: 11 |
| Binder: | | | | |
| Aqueous solution of sucrose fatty acid ester | HLB value: 11 | HLB value: 11 | | HLB value: 11 |
| Concentration (%) | 10 | 2.5 | 0 | 25 |
| Granulation temperature (°C.) | 65 | 45 | 45 | 45 |
| Grain size evaluation | xx | Δ | x | xx |
| Dispersibility and solubility | — | x | xx | — |
| Yield (%)** | — | 68.1 | 46.3 | — |

*90% or more passing a 150-mesh sieve.
**Ratio by weight of the amount of that part of SE granules obtained which does not pass a 150-mesh sieve to the amount of the starting SE material As is evident from the data in Table 1, the concentration of the aqueous SE solution and the granulation temperature were adequate in each of Examples 1–3, so that the products of Examples 1–3 were satisfactory in grain size as well as in dispersibility and solubility. Furthermore, said products were usable as food additives.

On the other hand, judging from the data shown in Table 2 for the comparative examples, the granulation temperature was excessively high in Comparative Example 1, so that the SE melted and could not be granulated. In Comparative Example 2, the concentration of the aqueous SE solution was too low and, accordingly, disintegration of granules took place in the step of granulation and drying; the product was inferior in grain size distribution as well as in dispersibility and solubility. In Comparative Example 3 in which water was used as the binding agent, the product was inferior in grain size distribution and in dispersibility and solubility to the product of Comparative Example 2. In Comparative Example 4, the concentration of the SE solution was excessively high, so that said solution could not be sprayed but fell in drops and collected on the bottom of the apparatus, where the SE powder caked.

We claim:

1. A method of producing sucrose fatty acid ester granules by the fluidized bed granulation and drying technique which comprises forming a fluidized bed comprising a sucrose fatty acid ester powder at a temperature not exceeding 60° C., spraying the fluidized bed with an aqueous sucrose fatty acid ester solution having a concentration of 3–20% by weight, as a binder, and then drying the sprayed fluidized bed, to thereby cause granulation.

* * * * *